United States Patent [19]

Diehl et al.

[11] 4,136,117

[45] Jan. 23, 1979

[54] PREPARATION OF 2,6-DINITROANILINES

[75] Inventors: Robert E. Diehl; Stephen D. Levy, both of Lawrenceville; William H. Gastrock, Hightstown, all of N.J.

[73] Assignee: American Cyanamid Company, Stamford, Conn.

[21] Appl. No.: 777,496

[22] Filed: Mar. 14, 1977

Related U.S. Application Data

[63] Continuation-in-part of Ser. No. 565,885, Apr. 7, 1975, abandoned, which is a continuation of Ser. No. 373,077, Jun. 25, 1973, abandoned.

[51] Int. Cl.² .................... C07C 85/24; C07C 85/26
[52] U.S. Cl. ........................... 260/577; 71/121; 260/573; 260/574; 260/576
[58] Field of Search ............... 260/577, 573, 574, 571, 260/576

[56] References Cited

U.S. PATENT DOCUMENTS

| 3,654,363 | 4/1972 | Pum et al. | 260/577 |
| 3,927,127 | 12/1975 | Damiano | 260/646 |

OTHER PUBLICATIONS

"Beilstein's Handbuch der Organischen Chemie", 4th Ed., vol. 12, p. 1010 (1929).
Houben–Weyl, "Methoden der Organischen Chemie", vol. X/1, 4th Ed., p. 647.
Porai-Koshits et al., "Chem. Ab.", Ab. No. 62:7606e (1965).
Smith, "Open–Chain Nitrogen Compounds", vol. II, p. 473 (1966).
Pinnow et al., "Berichte", vol. 31, p. 2518 (1898).

*Primary Examiner*—Winston A. Douglas
*Assistant Examiner*—John Doll
*Attorney, Agent, or Firm*—H. G. Jackson

[57] ABSTRACT

This invention relates to a novel process for the preparation of N-alkylated and N,N-dialkylated 2,6-dinitroaniline herbicidal agents.

18 Claims, 1 Drawing Figure

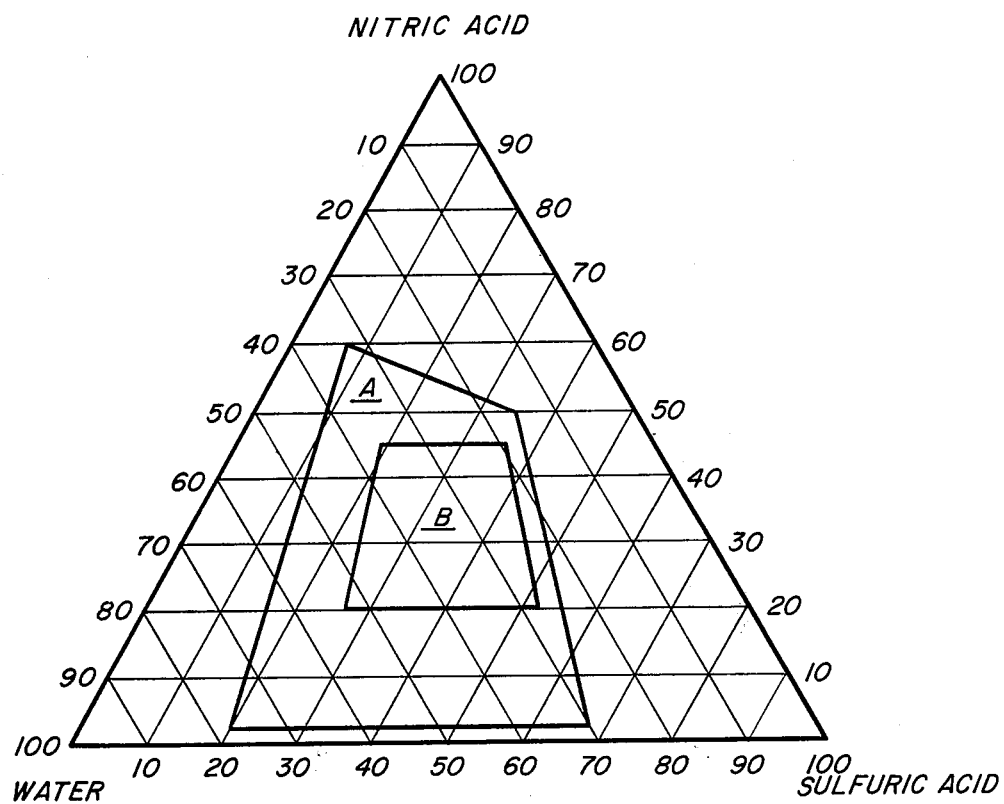

PREPARATION OF 2,6-DINITROANILINES

This is a Continuation-in-Part Application of copending United States Patent Application Ser. No. 565,885 filed Apr. 7, 1975, now abandoned which in turn is a Continuation Application of U.S. Application Ser. No. 373,077 filed June 25, 1973, now abandoned.

This invention relates to a novel process for the preparation of N-alkylated and N,N-dialkylated 2,6-dinitroanilines which are useful as herbicidal agents as disclosed in copending U.S. Patent Application Ser. No. 323,000, filed Jan. 12, 1973, now U.S. Pat. No. 3,920,742.

The N-alkylated and N,N-dialkylated 2,6-dinitroaniline compounds which are prepared by the novel process of this invention are represented by the formula:

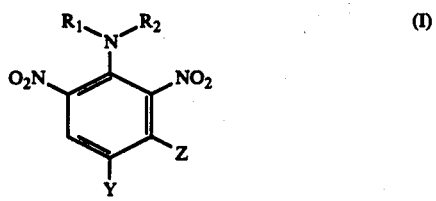

(I)

wherein Y represents alkyl $C_1$–$C_4$, halogen, $CF_3$; Z is hydrogen, halogen, alkyl $C_1$–$C_4$ or alkoxy $C_1$–$C_4$ and monosubstituted alkyl where the substituent is halogen, or alkoxy $C_1$–$C_4$; $R_1$ represents alkyl $C_1$–$C_6$ (straight or preferably branched), cycloalkyl $C_4$–$C_6$, monohaloalkyl $C_1$–$C_4$, or alkoxyalkyl where the alkyl group is $C_1$–$C_4$ and the alkoxy group is $C_1$–$C_4$; and $R_2$ is hydrogen or one of the groups of $R_1$.

Illustrative straight and branched alkyl substituents are methyl, ethyl, n-propyl, iso-propyl, n-butyl, t-butyl, n-pentyl, n-hexyl, 2-pentyl, 3-pentyl, sec-butyl, 1-ethylpropyl, and the like.

Illustrative cycloalkyl groups are cyclobutyl, cyclopentyl, and cyclohexyl groups.

Illustrative halogen substituents are fluoro, chloro, bromo and iodo groups.

The preparation of the compounds of formula I as disclosed in the prior art was accomplished by a nucleophilic displacement reaction between the appropriately substituted 2,6-dinitro-1-halo benzene and the appropriately substituted amine. The displacement reaction was effected by heating the reactants, preferably in an aromatic solvent, to between 50° C. and 150° C.

The preparation of N-alkylated-2,6-dinitroanilines of formula I in high yield by the nitration of N-alkylated-anilines is not disclosed in the prior art. Belgium Pat. No. 762,232 discloses a method for the preparation of 2,6-dinitro-tertiary-anilines, wherein both N-substituents are haloalkyl, by nitration with at least a five fold excess of nitric acid, which is present at the start of the reaction in a concentration of 50% to 90% and in an amount to leave an acid concentration of 50% at the end of the reaction, in the presence of a catalytic amount of nitrous acid or nitrite ion generating material.

The nitration of N-alkylated-secondary anilines in high yield in the 2 and 6 positions without prior blocking of the remaining hydrogen atom on the nitrogen, by acetylation for example, would be unexpected in this art.

We have discovered a safe and efficient process for the conversion of N-alkylated anilines of the formula II:

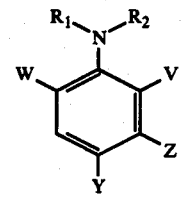

II wherein $R_1$, $R_2$, Y and Z are as defined for formula I above and W and V are hydrogen or nitro provided W and V are not both nitro; to N-alkylated-2,6-dinitroaniline compounds of formula I. In the process of this invention a compound of formula II is nitrated using the three component nitrating composition defined below and thereby converted in high yield to a mixture of a compound of formula I and where $R_2$ is H to the N-nitroso-N-alkylated-2,6-dinitroaniline. In the most preferred embodiment of this process the nitration mixture is further treated with a denitrosating agent to convert the N-nitroso by-product to the corresponding compound of formula I in those cases where it is necessary.

The nitrating agents employed in the process of the present invention are graphically represented by the trapezium A set forth in the annexed FIGURE; that is, compositions within the area defined by the lines connecting the points corresponding to: 60% $HNO_3$, 8% $H_2SO_4$, 32% $H_2O$; 50% $HNO_3$, 35% $H_2SO_4$, 15% $H_2O$; 2% $HNO_3$, 68% $H_2SO_4$, 30% $H_2O$ and 2% $HNO_3$, 20% $H_2SO_4$, 78% $H_2O$. Each of these values represents a real weight percent.

The preferred three component nitrating compositions fall within the trapezoid B shown in the annexed FIGURE. That is the area encompassed by the lines connecting the points corresponding to 45% $HNO_3$, 19% $H_2SO_4$, 36% $H_2O$; 45% $HNO_3$, 36% $H_2SO_4$, 19% $H_2O$; 20% $HNO_3$, 52% $H_2SO_4$, 28% $H_2O$ and 20% $HNO_3$, 27% $H_2SO_4$, 53% $H_2O$. Each of these values represents a real weight percent.

The optimum number of moles of nitric acid per mole of compound II will depend on the compound to be nitrated and composition of the nitrating agent employed. In general, the compounds of formula II wherein W and V are hydrogen are preferably nitrated using from 2.2 to 5.0 moles of nitric acid per mole of N-alkylated aniline. Within this broad range, the range of from 2.5 to 3.5 moles of nitric acid is generally more preferred. Where W or V is nitro, it is preferred to employ from 1.2 to 4.0 moles of nitric acid per mole of N-alkylated aniline. Within this range, the narrower range of from 1.5 to 2.5 moles of nitric acid is generally more preferred.

The mole ratio of sulfuric acid to N-alkylated aniline used in the nitrations of the present invention may advantageously range from 1.5:1 to 15.0:1, but preferably it ranges from 2.0:1 to 10.0:1. On a weight percentage basis, these ranges of sulfuric acid correspond to from about 30% to 70% with a preferred range from about 35% to 65%.

We have found that the amount of water present in the nitration mixture is an important factor in this invention and is related to the optimum temperature. In general reaction mixtures which contain higher percentages of water require higher reaction temperatures. The amount of water in the starting nitration mixture should be from about 15% to about 78% on the weight of the nitration mixture. A sufficiently high temperature should be employed to convert any N-alkylated-mononitroaniline to the N-alkylated-2,6-dinitroaniline. We have found that compounds of formula II can be nitrated at temperatures ranging from 0° C. to 70° C.; however, temperatures below about 15° C. tend to hinder completion of the dinitration and are thus not the most desirable. Temperatures above 70° C. are not desirable because the reaction becomes difficult to control. The reaction is exothermic and cooling is generally required to maintain the temperature below the upper limit and desirably within the optimum range. The optimum temperature will vary depending on the starting N-alkylated aniline employed and the composition of the nitrating agent. The generally preferred reaction temperature range is from about 35° C. to about 60° C.

When operating in the range of 0° C. to 70° C. (preferably 35° C. to 60° C.), the nitration with the mixed acid is easily controlled. We have found that nitration with concentrated nitric acid must be run below 10° C. or an uncontrolled reaction takes place. Due to the relatively simple control required for mixed acids, far less cooling capacity is required for that system. If power outages or shortages occur, the mixed acid nitration would be easily handled but with concentrated nitric acid an explosion would likely result.

Another feature of the mixed acid nitration is the small excess (0.50 to 1.50 moles) of nitric acid necessary to complete the reaction. With concentrated nitric acid, at least 5 to 10 moles are required. The cost and potential hazard with concentrated nitric acid would be far greater than with mixed acid where nitric acid recovery is not essential to the economics of the process.

In accordance with this invention the N-alkylated-aniline may be reacted with the nitrating solution as a liquid, solid, or dissolved in an inert solvent, such as ethylene dichloride, chloroform, carbon tetrachloride or nitromethane. In the practice of this invention we have found it preferable to utilize a solution of the N-alkylated aniline in ethylene dichloride wherein the ratio of milliliters of ethylene dichloride per gram of compound II ranges from about 3.0:1 to about 0.5:1, preferably 0.75:1.

The mode of addition is not a critical factor. One can add the nitrating agent to the starting compound II, or add compound II to the nitrating agent depending on the particular situation.

The product I may be isolated upon completion of the nitration reaction. The point of completion is determined by conventional methods such as thin layer chromatography or n.m.r. spectroscopy. However, we have also found that in the case of the formula II compounds wherein $R_2$ is hydrogen it is highly advantageous to further treat the reaction mixture from the nitration step with a denitrosating agent, preferably a combination of concentrated hydrochloric acid and sulfamic acid. This latter step is particularly important since such treatment results in increasing product yields by approximately the Formula III N-nitroso by-product present:

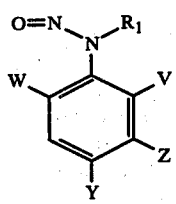

wherein $R_1$, V, W, Y and Z are as defined above. We have found that the mole ratios of hydrochloric acid and sulfamic acid to moles of N-nitroso compound present should be at least 1:1, in each case. Preferably, the mole ratio of hydrochloric acid to N-nitroso compound should be about 5:1 to 1.5:1. Preferably, the mole ratio of sulfamic acid to N-nitroso compound is 2:1. The temperature of the denitrosation step can range from 20° C. to 100° C. and should preferably be between 80° C. and 100° C. While the denitrosation step may be conducted at atmospheric pressure, it is preferable to carry out this step under pressure to conserve hydrochloric acid.

Other denitrosating agents such as hydrochloric acid and ferrous chloride may also be employed in this process; however, the use of hydrochloric acid and sulfamic acid is preferred.

While the preferred method of this invention is carried out ordinarily by a batch process, a continuous process is also contemplated.

Illustrative compounds which are readily prepared by the procedure of this invention include, for example: N-(isopropyl)-3,4-dimethyl-2,6-dinitroaniline; N-n-propyl-3,4-dimethyl-2,6-dinitroaniline; N-cyclohexyl-3,4-dimethyl-2,6-dinitroaniline; N-(2-butyl)-3,4-dimethyl-2,6-dinitroaniline; N-cyclopentyl-3,4-dimethyl-2,6-dinitroaniline; N-cyclobutyl-3,4-dimethyl-2,6-dinitroaniline; N-(2-butyl)-3-isopropyl-4-methyl-2,6-dinitroaniline; N-(2-butyl)-4-t-butyl-2,6-dinitroaniline; N-(2-amyl)-3-sec-butyl-4-methyl-2,6-dinitroaniline; N-isopropyl-3,4-diethyl-2,6-dinitroaniline; N-3-pentyl-3,4-diethyl-2,6-dinitroaniline; N-(2-butyl)-3-chloro-4-methyl-2,6-dinitroaniline; N-(2-butyl)-3-methoxy-4-methyl-2,6-dinitroaniline; N-(1-ethylpropyl)-3,4-dimethyl-2,6-dinitroaniline.

The 3,4-diethyl derivatives, 3-methyl-4-ethyl derivatives, 3-ethyl-4-methyl, 3-ethyl-4-propyl, 3,4-diisopropyl, 3,4-di-n-propyl, 3,4-di-n-butyl, 3,4-diisobutyl, 3-propyl-4-butyl, and 3-methyl-4-isopropyl derivatives of the abovenamed 2,6-di-nitroanilines, are likewise prepared by the above procedure, utilizing the appropriate 3,4-disubstituted-N-substituted anilines.

Illustrative compounds wherein Y is $CF_3$ include, for example: N-n-propyl-3-methyl-2,6-dinitro-4-(trifluoromethyl)aniline; N-sec-butyl-3-methyl-2,6-dinitro-4-(trifluoromethyl)aniline; 3-methyl-2,6-dinitro-N-3-pentyl-4-(trifluoromethyl)aniline; and 3-ethyl-2,6-dinitro-N-isopropyl-4-(trifluoromethyl)aniline.

Illustrative 2,6-dinitro-tertiary-anilines which are prepared by the process of this invention include, for example: N-methyl-N-(2-chloroethyl)-3,4-dimethyl-2,6-dinitroaniline; N,N-di(n-propyl)-α,α,α-trifluoro-2,6-dinitro-p-toluidine; N-ethyl-N-butyl-α,α,α-trifluoro-2,6-dinitro-p-toluidine; N,N-di(n-propyl)-3,4-dimethyl-2,6-dinitroaniline; N,N-dimethyl-3,4-dimethyl-2,6-dinitroaniline; N,N-diethyl-3,4-dimethyl-2,6-dinitroaniline; N-ethyl-N-butyl-3,4-dimethyl-2,6-dinitroaniline; N-methyl-N-cyclohexyl-3,4-dimethyl-2,6-dinitroaniline; N,N-diethyl-4-chloro-3-methyl-2,6-dinitroaniline; N,N-dibutyl-3,4-dimethyl-2,6-dinitroaniline; N,N-di(n-propyl)-4-chloro-3-methyl-2,6-dinitroaniline; N,N-di(n-propyl)-3-chloro-4-methyl-2,6-dinitroaniline; N,N-dimethyl-3-methyl-4-chloro-2,6-dinitroaniline; N-methyl-N-ethyl-3,4-dimethyl-2,6-dinitroaniline; N,N-dimethyl-3,4-dimethyl-α⁴,α⁴,α⁴-trifluoro-2,6-dinitroaniline; N,N-diethyl-3-chloro-4-methyl-2,6-dinitroaniline; N,N-di(n-propyl)-3,4-dimethyl-α⁴,α⁴,α⁴-trifluoro-2,6-dinitroaniline; N,N-di(n-propyl)-3-methoxy-4-methyl-2,6- dinitroaniline; N,N-diethyl-3,4-dimethyl-α⁴,α⁴,α⁴-trifluoro-2,6-dinitroaniline; N,N-diethyl-3-methoxy-4-methyl-2,6-dinitroaniline; N,N-di(n-propyl)-3-ethoxy-4-methyl-2,6-dinitroaniline; N,N-di(n-propyl)-3-butoxy-4-methyl-2,6-dinitroaniline; N,N-bis(2-chloroethyl)-3,4-dimethyl-2,6-dinitroaniline; and N,N-bis(2-chloroethyl)-4-methyl-2,6-dinitroaniline.

Some of the preferred methods for making preferred dinitroanilines are set forth below.

In a preferred method for nitrating N-(1-ethylpropyl)-3,4-dimethylaniline, the nitrating agent employed has a water content from about 35% to 53% by weight and the aniline compound is reacted in an amount to give a mole ratio of nitric acid to said aniline of about 3.25:1 and a mole ratio of sulfuric acid to said aniline compound of about 2.25:1. The reaction is conducted while maintaining the temperature of the reaction mixture from about 35° C. to 70° C. The reactants are mixed over a period of about 2 hours, maintaining the temperature of said reaction mixture from about 35° C. to about 70° C. for about 1 hour on completion of said mixing. Thereafter, denitrosation is effected by adding to the mixture hydrochloric acid and sulfamic acid, maintaining a temperature of 70° C. to 100° C. over a period of 1 to 6 hours and recovering the N-(1-ethylpropyl)-2,6-dinitro-3,4-dimethylaniline product formed.

The process is preferably conducted in an ethylene dichloride solvent, further characterized in that the solvent ratio expressed in milliliters of ethylene dichloride per gram of N-(1-ethylpropyl)-3,4-dimethylaniline ranges from about 3.0:1.0 to 0.5:1.0, more preferably from about 0.75:1.0.

In a preferred method for the nitration of N-(2-butyl)-3,4-dimethylaniline, the nitrating agent has a water content from about 40% to 53% by weight, and the aniline compound is reacted in an amount to give a mole ratio of nitric acid to said aniline compound of about 3.25:1 and a mole ratio of sulfuric acid to said aniline compound of about 2.25:1, maintaining the temperature of the reaction mixture from about 50° C. to 70° C. while the reactants are mixed therein over a period of about 2 hours, thereafter maintaining the temperature of said reaction mixture from about 50° C. to about 70° C. for about 1 hour on completion of said mixing. Denitrosation of the mixture is effected by adding hydrochloric acid and sulfamic acid thereto, maintaining a temperature of 70° C. to 100° C. over a period of 1 to 6 hours and recovering the N-(2-butyl)-2,6-dinitro-3,4-dimethylaniline product produced thereby.

The process is preferably conducted in an ethylene dichloride solvent, further characterized in that the solvent ratio expressed in milliliters of ethylene dichloride per gram of N-(2-butyl)-3,4-dimethylaniline ranges from about 3.0:1.0 to about 0.5:1.0, more preferably from 0.75 to 1.0.

The process of the present invention is further illustrated in the examples below which are not to be taken as being limitative thereof. In each case, the parts and percentages specified herein are by weight unless otherwise indicated. In all cases the final product was isolated by thin layer chromatography, and assayed by ultraviolet absorption spectroscopy.

EXAMPLE 1

Nitration of N-(1-Ethylpropyl)-3,4-Dimethylaniline

To a solution of mixed acid prepared by adding 145.2 g. of 70.5% nitric acid (1.625 moles) and 116.6 g. of 94.5% sulfuric acid (1.125 moles) to 58.8 g. of water, a solution of 101.0 g. of 94.6% N-(1-ethylpropyl)-3,4-dimethylaniline (0.5 mole) in 143.5 mls. of ethylene dichloride was added over a period of 2 hours at 35° C. The reaction was maintained at 35° C. for one hour and the aqueous phase was then separated. The organic phase was washed successively with 300 mls. of 5% caustic solution and 300 mls. of water. The organic solution was dried over anhydrous magnesium sulfate, filtered and concentrated at 70° C. under vacuum to obtain 141.5 g. of crude product containing 117 g. (82.6%) N-(1-ethylpropyl)-3,4-dimethyl-2,6-dinitroaniline and 14.2 g. (10.0%) of N-nitroso-N-(1-ethylpropyl)-3,4-dimethyl-2,6-dinitroaniline. The total yield of the desired 2,6-dinitroaniline is 72.6%.

EXAMPLES 2–10

Nitration of N-(1-Ethylpropyl)-3,4-Dimethylaniline

These examples show the results obtained when N-(1-ethylpropyl)-3,4-dimethylaniline was nitrated at 35° C. in reaction mixtures containing the same mole ratios of nitric and sulfuric acid to starting material but different water contents. In all cases the general reaction conditions were the same as those employed in Example 1. In some cases the starting material was added without solvent and the reaction mixtures were subsequently extracted with toluene or xylene and worked up in the usual manner. The results are recorded in Table I.

TABLE I

| | Nitration of N-(1-Ethylpropyl)3,4-Dimethylaniline (A) | | | | | | | |
|---|---|---|---|---|---|---|---|---|
| | Reaction Mixture | | | Product Composition | | Yields | | |
| Example Number | HNO₃ (M) A (M) | H₂SO₄ (M) A (M) | % H₂O | % N-Nitroso[a] | % B[b] | % N-Nitroso[a] | % B[b] | % Total |
| 2 | 3.0 | 2.0 | 27.0 | 48.6 | 43.1 | 41.2 | 40.3 | 81.5 |
| 3 | 3.0 | 2.0 | 31.1 | 31.9 | 61.0 | 29.5 | 48.0 | 77.5 |
| 4 | 3.0 | 2.0 | 35.6 | 13.6 | 81.0 | 12.2 | 78.5 | 90.7 |
| 5 | 3.0 | 2.0 | 40.4 | 19.1 | 81.0 | 16.0 | 74.6 | 90.6 |
| 6 | 3.5 | 2.5 | 23.6 | 74.8 | 20.3 | 62.3 | 18.8 | 81.1 |
| 7 | 3.5 | 2.5 | 31.7 | 15.2 | 81.4 | 13.6 | 80.3 | 93.9 |
| 8 | 2.5 | 1.5 | 21.8 | 48.9 | 30.5 | 40.8 | 28.1 | 68.9 |
| 9 | 2.5 | 1.5 | 30.0 | 33.1 | 56.0 | 27.5 | 51.3 | 78.8 |
| 10 | 2.5 | 1.5 | 34.8 | 14.5 | 81.0 | 12.4 | 76.5 | 88.9 |

[a]N-nitroso-N-(1-ethylpropyl)-3,4-dimethyl-2,6-dinitroaniline
[b]B=N-(1-ethylpropyl)-3,4-dimethyl-2,6-dinitroaniline

EXAMPLES 11–13

Nitration of N-(1-Ethylpropyl)-3,4-Dimethylaniline

The following examples show that nitration of N-(1-ethylpropyl)-3,4-dimethylaniline at 20°–25° C. in mixtures that contain 16.7, 21.7, and 48.7 percent water, respectively, results in low yields of both N-(1-ethylpropyl)-3,4-dimethyl-2,6-dinitroaniline and N-nitroso-N-(1-ethylpropyl)-3,4-dimethyl-2,6-dinitroaniline. This example shows influence of mole ratios and water content on the yields and product compositions.

The general procedure employed was the same as that described in Example 1 using the quantities indicated in Table II starting with 4.86 g. of N-(1-ethylpropyl)-3,4-dimethylaniline in 15 ml. of ethylene dichloride. In all cases the addition time was two hours and the hold time was one hour.

for six hours, 2-liters of water was added thereto and the aqueous phase was separated. The aqueous phase was extracted with 500 ml. of ethylene dichloride and the organic phases were combined. The combined organic phase was washed with 3-liters of water, the aqueous phase separated and the ethylene dichloride was removed under vacuum at 68° C. to recover 1915 g. of product containing 1820 g. of 2,6-dinitro-N-(1-ethylpropyl)-3,4-dimethylaniline and less than 0.1% of 2,6-dinitro-N-nitroso-N-(1-ethylpropyl)-3,4-dimethylaniline.

TABLE II

| | Nitration of N-(1-Ethylpropyl)-3,4-dimethylaniline (A) at 20–25° C. | | | | | | | |
|---|---|---|---|---|---|---|---|---|
| | Reaction Mixture | | | Product Composition | | Yields | | |
| Example Number | $HNO_3$ (m) A (m) | $H_2SO_4$ (m) A (m) | % $H_2O$ | % N-Nitroso-[a] | % B[b] | % N-Nitroso[a] | % B[b] | % Total |
| 11 | 1.5 | 2.0 | 48.4 | 0 | 0 | 0 | 0 | 0 |
| 12 | 2.2 | 2.0 | 16.7 | 29.4 | 42.7 | 21.1 | 33.8 | 54.9 |
| 13 | 5.0 | 3.5 | 21.7 | 74.2 | 0 | 61.7 | 0 | 61.7 |

[a]N-Nitroso-N-(1-ethylpropyl)-3,4-dimethyl-2,6-dinitroaniline
[b]B=N-(1-ethylpropyl)-3,4-dimethyl-2,6-dinitroaniline

EXAMPLES 14–15

Examples 14 and 15, shown in Table III, show the influence of higher temperatures and water contents on the product composition and total yield. The general conditions employed were the same as in Example 1, with the exceptions noted. The compositions are described in terms of moles (m) and grams (g).

EXAMPLES 17–24

The following examples of the denitrosation of crude nitration products from the nitration of N-(1-ethylpropyl)-3,4-dimethylaniline, shown in Table IV, were carried out using the general conditions described in Example 16. The mole ratios shown in Table IV express

TABLE III

| | Nitration of N-(1-Ethylpropyl)-3,4-dimethylaniline (A) | | | | | | | |
|---|---|---|---|---|---|---|---|---|
| | Reaction Mixtures | | | | | Yields | | |
| Example Number | $HNO_3$ (m) A (m) | $H_2SO_4$ (m) A (m) | % $H_2O$ | EDC[a] (m) A (g) | Temperature °C. | % N-Nitroso[b] | % B[c] | % Total |
| 14 | 3.25 | 2.25 | 43.3 | 0.75 | 60 | 23.5 | 64.5 | 88.0 |
| 15 | 3.25 | 2.25 | 49.1 | 0.75 | 70 | 13.5 | 73.5 | 87.0 |

[a]EDC = ethylene dichloride
[b]N-nitroso-N-(1-ethylpropyl)-3,4-dimethyl-2,6-dinitroaniline
[c]B = N-(1-ethylpropyl)-3,4-dimethyl-2,6-dinitroaniline

EXAMPLE 16

Denitrosation of Crude Nitration Product from N-(1-Ethylpropyl)-3,4-dimethylaniline To a crude nitration solution comprising 1550 g. of 2,6-dinitro-N-(1-ethylpropyl)-3,4-dimethylaniline and 340 g. of 2,6-dinitro-N-nitroso-N-(1-ethylpropyl)-3,4-dimethylaniline in 3700 mls. of ethylene dichloride was added 212 g. of sulfamic acid and 2850 mls. of 37.7% hydrochloric acid. The mixture was refluxed at 80° C.

the number of moles of reagent per mole of N-nitroso by-product. In most cases the reactions were conducted in an autoclave.

TABLE IV

| | Denitrosation of Crude Nitration Products from N-(1-Ethylpropyl)-3,4-dimethylaniline | | | | | |
|---|---|---|---|---|---|---|
| | Reaction Mixture | | | | Reaction | |
| Example Number | HCl(m) N-Nitroso[a](m) | $H_2NSO_3H$(m) N-Nitroso[a](m) | Solvent (mls) | Temp. °C. | Period Hours | % Yield[f] |
| 17 | 17.2 | 2.0 | 10[b] | 80 | 5 | 90.0 |
| 18 | 5.1 | 1.5 | 60[c] | 100[e] | 2 | 97.0 |
| 19 | 5.1 | 1.5 | 60[b] | 80[e] | 6 | 94.3 |
| 20 | 5.1 | 1.5 | 60[c] | 80[e] | 6 | 97.0 |
| 21 | 3.1 | 1.5 | 60[b] | 80[e] | 6 | 97.2 |
| 22 | 3.1 | 2.4 | 50[b] | 70[e] | 6 | 95.5 |
| 23 | 2.5 | 2.1 | 50[d] | 80[e] | 1 | 96.4 |
| 24 | 2.5 | 2.1 | 15 | 80[e] | 6 | 96.5 |

[a]N-nitroso-N-(1-ethylpropyl)-2,6-dinitro-3,4-dimethylaniline
[b]Ethylene dichloride
[c]Toluene
[d]n-Propanol
[e]Reaction conducted in autoclave
[f]In all cases the percentage of N-nitroso-N-(1-ethylpropyl)-3,4-dimethyl-2,6-dinitroaniline in the final product was less than 0.1% by weight

EXAMPLE 25

Nitration of N-(2-Butyl)-3,4-dimethylaniline

To a solution of mixed acid prepared by adding 134.1 g. of 70.5% nitric acid (1.50 moles) and 101.1 g. of 96.9% sulfuric acid (1.00 mole) to 87.2 g. of water at 50°

C.-55° C., a solution of 92.3 g. of 95.9% N-(2-butyl)-3,4-dimethylaniline in 66.5 mls. of ethylene dichloride was added over a period of 2 hours. The reaction was held at 55° C. for an additional hour and the aqueous phase was then separated.

The organic phase was washed successively with 500 mls. of a 5% aqueous caustic solution and 500 mls. of water. The organic phase was then dried over anhydrous magnesium sulfate, filtered and concentrated at 70° C. under vacuum to obtain 130.0 g. of crude product containing 100 g. (75.5% yield) of 2,6-dinitro-N-(2-butyl)-3,4-dimethylaniline and 22.0 g. (14.9% yield) of 2,6-dinitro-N-nitroso-N-(2-butyl)-3,4-dimethylaniline. The total yield of the desired 2,6-dinitroaniline product was 90.4%.

EXAMPLES 26-28

The examples shown in Table V of the nitration of N-(2-butyl)-3,4-dimethylaniline illustrate the influence of water content of the nitration mixture on the product composition. That is to say that the use of a mixed acid containing higher water content and a lower mole ratio of nitric acid leads to a lower percentage of by-product N-nitroso compound.

In all cases the general procedure of Example 1 was employed at 35° C., adding a solution of 4.53 g. of N-(2-butyl)-3,4-dimethylaniline in 15 mls. of ethylene dichloride as the starting material over a period of two hours and then holding the reaction at 35° C. for an additional hour.

thylaniline and 6.84 g. of 2,6-dinitro-N-nitroso-N-(2-butyl)-3,4-dimethylaniline in 15 mls. of ethylene dichloride was added 3.94 g. of sulfamic acid and 9.84 g. of 37.6% hydrochloric acid. The mixture was stirred and heated for six hours, under pressure, at 80° C. and at the end of this period 20 mls. of water was added and the pH of the mixture was adjusted to 9-11 by careful addition of a 50% aqueous sodium hydroxide solution. The phases were allowed to separate and the aqueous layer was removed. The organic layer was washed with 20 ml. of water, dried over anhydrous magnesium sulfate, filtered and concentrated under vacuum at 70° C. to obtain 28.2 g. containing 24.6 g. (93% yield) of 2,6-dinitro-N-(2-butyl)-3,4-dimethylaniline and less than 0.1% of 2,6-dinitro-N-nitroso-N-(2-butyl)-3,4-dimethylaniline.

EXAMPLE 33

An acid solution was prepared by mixing 1.83 gms. water, 6.83 g. of 96.9% sulfuric acid (0.0675 moles) and 8.71 g. of 70.5% nitric acid (0.0975 mole). To this solution was added a solution of 5.93 g. (0.03 mole) N-2-butyl-3-chloro-4-methylaniline in 4 g. of ethylene dichloride over a period of 75 minutes at 35° C.-40° C. The mixture was heated for 2.25 hours at 40° C.-45° C. an additional 0.75 hour at 55° C. The mixture was diluted with ethylene dichloride and washed with a dilute aqueous caustic solution (to pH 10-11), washed with fresh water, dried over magnesium sulfate and filtered. Upon concentrating there was obtained 7.8 g. of oil.

TABLE V

| | Nitration of N-(2-Butyl)-3,4-Dimethylaniline (C) | | | | | | | |
|---|---|---|---|---|---|---|---|---|
| | Reaction Mixture | | | Product Composition | | Yield | | |
| Example Number | $\frac{HNO_3(m)}{C\ (m)}$ | $\frac{H_2SO_4(m)}{C\ (m)}$ | $H_2O$ % | % N-nitroso[a] | % Dinitro[b] | % N-nitroso[a] | % Dinitro[b] | % Total |
| 26 | 4.0 | 2.0 | 20.6 | 70.8 | 21.4 | 54.3 | 18.2 | 72.5 |
| 27 | 3.5 | 2.5 | 27.6 | 19.8 | 70.6 | 16.7 | 66.6 | 83.3 |
| 28 | 3.5 | 2.5 | 31.7 | 10.5 | 76.3 | 8.9 | 72.0 | 80.9 |

[a]N-nitroso-N-(2-butyl)-2,6-dinitro-3,4-dimethylaniline
[b]N-(2-butyl)-2,6-dinitro-3,4-dimethylaniline

EXAMPLES 29-31

The examples of Table VI show the variation in total yield and product composition due to modifications in water content and temperature of the reaction mixture in the nitration of N-(2-butyl)-3,4-dimethylaniline. These results indicate a preferred temperature of about 50° C. and a water content of about 40% for the nitration of N-(2-butyl)-3,4-dimethylaniline with the stoichiometry shown.

This oil on examination by thin layer chromatography was found to contain one major and three minor components.

The oil was dissolved in 20 ml. of ethylene dichloride and to the solution was added 13 ml. concentrated hydrochloric acid and 1 g. of sulfamic acid. The mixture was heated under reflux seven hours and examination of an aliquot by thin layer chromatography showed that one of the three minor components in the original oil had disappeared. The mixture was cooled and the aque-

TABLE VI

| | Reaction Mixture | | | | | Yield | | |
|---|---|---|---|---|---|---|---|---|
| Example Number | $\frac{HNO_3(m)}{C^{(a)}\ (m)}$ | $\frac{H_2SO_4(m)}{C\ (m)}$ | % $H_2O$ | $\frac{EDC^{(b)}(ml.)}{C\ (g)}$ | Temperature °C. | % N-Nitroso[c] | % D[d] | % Total |
| 29 | 3.25 | 2.25 | 38.8 | 0.75 | 50 | 15.3 | 73.3 | 88.6 |
| 30 | 3.25 | 2.25 | 43.8 | 0.75 | 60 | 18.1 | 68.9 | 87.0 |
| 31 | 3.25 | 2.25 | 49.1 | 0.75 | 70 | 20.7 | 65.0 | 85.7 |

[a]C = N-(2-butyl)-3,4-dimethylaniline
[b]EDC = ethylene dichloride
[c]N-nitroso-N-(2-butyl)-2,6-dinitro-3,4-dimethylaniline
[d]D = N-(2-butyl)-2,6-dinitro-3,4-dimethylaniline

EXAMPLE 32

Denitrosation of Crude Nitration Product from N-(2-Butyl)-3,4-Dimethylaniline To a solution of 30 grams crude nitration product comprising 20.2 g. of 2,6-dinitro-N-(2-butyl)-3,4-dimeous layer discarded. The organic layer was washed with water, dried over magnesium sulfate, filtered and concentrated to obtain 5.7 g. of oil. The major component of this oil was separated in a pure state by liquid chromatography and was shown by proton magnetic resonance spectroscopy to be the desired N-(2-butyl)-2,6-dinitro-3-chloro-p-toluidine.

EXAMPLE 34

An acid solution was prepared by mixing 2.55 g. of water, 6.91 g. of 95.7% sulfuric acid and 8.71 g. of 70.5% nitric acid. To this solution was added over about two hours a solution of 6.3 g. N-2-butyl-4-t-butylaniline in 19 ml. of ethylene dichloride at 33° C.-37° C. The reaction mixture was stirred 1.5 hours at 40° C.-45° C. and one hour at 50° C. An additional 1.93 g. of 95.3% sulfuric acid was added and the mixture was stirred 0.5 hour more at 50° C. Tests showed that no unreacted N-2-butyl-4-t-butylaniline or its mono-nitro derivative remainded in the reaction mixture. The mixture was cooled, the organic phase was separated and washed with dilute aqueous caustic solution and then with water. To the organic phase was then added 13 ml. of concentrated hydrochloric acid and 1.0 g. of sulfamic acid. This mixture was heated under reflux for four hours, then it was cooled and the acid layer discarded. The organic phase was washed with water and concentrated to obtain 14.4 g. of an oil. This oil was placed on a silica gel column and eluted with toluene. The fastest moving component was extracted from the silica using methylene chloride. The extract was concentrated to obtain 3.4 g. (over 38% of theory) of yellow solid which was identified as N-2-butyl-2,6-dinitro-4-t-butylaniline.

EXAMPLE 35

Preparation of N-Sec-butyl-2-nitro-3,4-dimethylaniline and N-Sec-butyl-6-nitro-3,4-dimethylaniline N-Sec-butyl-3,4-dimethylaniline (5.3 g., 0.03 mole) is dissolved in 10 ml. of dichloroethane and carefully treated with mixed acids (6 ml. concentrated sulfuric acid and 2.7 g. concentrated nitric acid) at 15° C.-25° C. When the addition is complete, the mixture is poured into water. The organic layer is separated and purified by column chromatography on silica gel using hexane as eluent. The first compound to elute is N-sec-butyl-2-nitro-3,4-dimethylaniline and is identified by its n.m.r. and IR spectra. The second compound to be eluted is N-sec-butyl-6-nitro-3,4-dimethylaniline which is also characterized by its n.m.r. spectrum.

EXAMPLE 36

Preparation of N-(1-Ethylpropyl)-2,6-dinitro-3,4-dimethylaniline

N-(1-Ethylpropyl)-2-nitro-3,4-dimethylaniline is prepared by the procedure of Example 35 substituting N-(1-ethylpropyl)-3,4-dimethylaniline for the N-sec-butyl-3,4-dimethylaniline used therein. The desired 2,6-dinitro compound is prepared in good yield and purity by nitrating the 2-nitro compound using the procedure of Example 1.

EXAMPLE 37

In a manner similar to Example 36 N-(1-ethylpropyl)-6-nitro-3,4-dimethylaniline is prepared by the procedure of Example 35 substituting N-(1-ethylpropyl)-3,4-dimethylaniline for the N-sec-butyl-3,4-dimethylaniline used therein. The 6-nitro compound is converted into N-(1-ethylpropyl)-2,6-dinitro-3,4-dimethylaniline using the procedure of Example 1.

EXAMPLE 38

A mixed acid solution was prepared by adding 95.3% sulfuric acid (5.79 g.; 0.056 mole) and 70.5% nitric acid (7.27 g.; 0.081 mole) to water (1.27 g.). To the mixed acids was added, while stirring, a solution of N,N-bis-(2-chloroethyl)-3,4-dimethylaniline (6.15 g.; 0.025 mole) in 15 ml. of ethylene dichloride. The addition was made over a period of 90 minutes at a temperature of 35° C. to 45° C. Upon completion of the addition, the mixture was stirred an additional 2 hours at 30° C. to 40° C., and the lower layer was then separated and discarded. The upper layer was washed with 10 ml. portions of dilute caustic solution and water, in that order. The organic solution was dried over anhydrous magnesium sulfate and then chromatographed on a column of silica gel. Elution with benzene permitted the isolation of 3.73 g. (44.5%) of a yellow solid, which was shown by nuclear magnetic resonance spectroscopy as N,N-bis-(2-chloroethyl)-2,6-dinitro-3,4-dimethylaniline.

We claim:

1. A method for the manufacture of a compound of the formula:

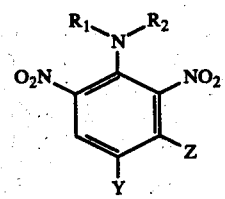

wherein Y is alkyl $C_1$-$C_4$, halogen or $CF_3$; Z is hydrogen, halogen, alkyl $C_1$-$C_4$, alkoxy $C_1$-$C_4$, monohaloalkyl $C_1$-$C_4$, or monoalkoxy ($C_1$-$C_4$) alkyl ($C_1$-$C_4$); $R_1$ represents alkyl $C_1$-$C_6$, cycloalkyl $C_4$-$C_6$, monohaloalkyl $C_1$-$C_4$ or alkoxyalkyl where the alkyl group is $C_1$-$C_4$ and the alkoxy group is $C_1$-$C_4$; $R_2$ is hydrogen or one of the groups of $R_1$; comprising reacting an N-alkylated aniline of the formula:

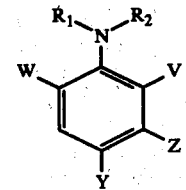

wherein $R_1$, $R_2$, Y and Z are as defined above and W and V are hydrogen or nitro provided W and V are not both nitro; with a three-component nitrating agent having a composition with the following limits: 60% $HNO_3$, 8% $H_2SO_4$, 32% $H_2O$; 50% $HNO_3$, 35% $H_2SO_4$, 15% $H_2O$; 2% $HNO_3$, 68% $H_2SO_4$, 30% $H_2O$; 2% $HNO_3$, 20% $H_2SO_4$, 78% $H_2O$; at a temperature in the range of from 0° C. to 70° C.; further characterized in that, when W and V are hydrogen in the N-alkylated aniline, from 2.2 to 5.0 moles of nitric acid are employed per mole of the N-alkylated aniline and, when one of W and V in the N-alkylated aniline is nitro, the moles of nitric acid per mole of N-alkylated aniline is in the range of 1.2 to 4.0 moles and when a compound of the formula:

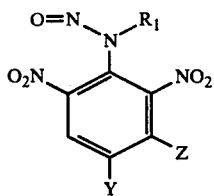

wherein $R_1$ Y and Z are as defined above is formed in the reaction mixture denitrosating the reaction mixture.

2. A method according to claim 1 wherein the nitrating reagent is a composition within the limits of 45% $HNO_3$, 19% $H_2SO_4$, 36% $H_2O$; 45% $HNO_3$, 36% $H_2SO_4$, 19% $H_2O$: 20% $HNO_3$, 52% $H_2SO_4$, 28% $H_2O$; 20% $HNO_3$, 27% $H_2SO_4$, 53% $H_2O$.

3. A method according to claim 1 wherein the temperature is in the range of from about 35° C. to about 60° C.

4. A method according to claim 1 wherein the N-alkylated aniline is N-(1-ethylpropyl)-3,4-dimethylaniline.

5. A method according to claim 1 wherein the N-alkylated aniline is N-(2-butyl)-3,4-dimethylaniline.

6. A method according to claim 1 wherein $R_2$ is hydrogen further characterized by the step of denitrosating the reaction mixture formed therein by reacting the reaction mixture with 1 mole of concentrated hydrochloric acid and 1 mole of sulfamic acid per mole of any N-nitroso compound present.

7. A method according to claim 6 wherein the mole ratio of hydrochloric acid to N-nitroso compound is between 5:1 and 3:1.

8. A method according to claim 1 wherein the mole ratio of sulfamic acid present in the reaction mixture to the N-nitroso compound present in the reaction mixture is 2:1.

9. A method according to claim 1 wherein W and V are hydrogen in the N-alkylated aniline and a range of from 2.5 to 3.5 moles of nitric acid are employed per mole of said N-alkylated aniline.

10. A method according to claim 1 wherein W or V in the N-alkylated aniline is nitro and the moles of nitric acid per mole of N-alkylated aniline is in the range of 1.5 to 2.5.

11. A method according to claim 1 wherein the mole ratio of sulfuric acid to N-alkylated aniline is in the range of from 1.5:1 to 15.0:1.

12. A method according to claim 10 wherein the range is from 2.0:1 to 10.0:1.

13. A method for the nitration of N-(1-ethylpropyl)-3,4-dimethylaniline according to claim 1 wherein the nitrating agent has a water content from about 35% to 53% by weight and the aniline compound is reacted in an amount to give a mole ratio of nitric acid to said aniline of about 3.25:1 and a mole ratio of sulfuric acid to said aniline compound of about 2.25:1, maintaining the temperature of the reaction mixture from about 35° C. to 70° C. while the reactants are mixed therein over a period of about 2 hours, maintaining the temperature of said reaction mixture from about 35° C. to about 70° C. for about 1 hour on completion of said mixing, separating the spent acid from the organic mixture, adding a denitrosating mixture of hydrochloric acid and sulfamic acid to the organic mixture, maintaining a temperature of 70° C. to 100° C. over a period of 1 to 6 hours and recovering the N-(1-ethylpropyl)-2,6-dinitro-3,4-dimethylaniline product therefrom.

14. A method according to claim 13 wherein the nitration is conducted in an ethylene dichloride solvent, further characterized in that the solvent ratio expressed in milliliters of ethylenedichloride per gram of N-(1-ethylpropyl)-3,4-dimethylaniline ranges from about 3.0:1.0 to 0.5:1.0.

15. A method according to claim 14 wherein the solvent ratio is from about 0.75:1.0.

16. A method for the nitration of N-(2-butyl)-3,4-dimethylaniline according to claim 1 wherein the nitrating agent has a water content from about 40% to 53% by weight, wherein said aniline compound is reacted in an amount to give a mole ratio of nitric acid to said aniline compound of about 3.25:1 and a mole ratio of sulfuric acid to said aniline compound of about 2.25:1, maintaining the temperature of the reaction mixture from about 50° C. to 70° C. while the reactants are mixed therein over a period of about 2 hours, maintaining the temperature of said reaction mixture from about 50° C. to about 70° C. for about 1 hour on completion of said mixing, separating the spent acid from the organic mixture, adding a denitrosating mixture of hydrochloric acid and sulfamic acid to the organic mixture, maintaining a temperature of 70° C. to 100° C. over a period of 1 to 6 hours and recovering the N-(2-butyl)-2,6-dinitro-3,4-dimethylaniline product therefrom.

17. A method according to claim 16 wherein the nitration is conducted in an ethylene dichloride solvent, further characterized in that the solvent ratio expressed in milliliters of ethylene dichloride per gram of N-(2-butyl)-3,4-dimethylaniline ranges from about 3.0:1.0 to about 0.5:1.0.

18. A method according to claim 17 wherein the solvent ratio is from about 0.75:1.0.

* * * * *